United States Patent [19]

Peter et al.

[11] Patent Number: 5,512,692
[45] Date of Patent: Apr. 30, 1996

[54] PROCESS FOR REMOVING GLYCEROL FROM GLYCERIDES

[75] Inventors: Siegfried Peter, Lindenweg 3, 8525, Uttenreuth-Weiher; Bernd Czech; Eckard Weidner, both of Erlangen, all of Germany

[73] Assignee: Siegfried Peter, Uttenreuth-Weiher, Germany

[21] Appl. No.: 320,770

[22] Filed: Oct. 11, 1994

Related U.S. Application Data

[63] Continuation of Ser. No. 891,722, Jun. 1, 1992, abandoned.

[30] Foreign Application Priority Data

Jun. 5, 1991 [DE] Germany .................. 41 18 487.4

[51] Int. Cl.[6] ................................................. C11B 7/00
[52] U.S. Cl. .................. 554/210; 554/206; 554/207; 554/14; 554/17; 554/209
[58] Field of Search ................ 554/14, 209, 210, 554/206, 207

[56] References Cited

U.S. PATENT DOCUMENTS

| 4,345,976 | 8/1982 | Peter et al. ............................. 554/207 |
| 5,110,509 | 5/1992 | Peter et al. ............................. 554/210 |

*Primary Examiner*—José G. Dees
*Assistant Examiner*—Deborah D. Carr
*Attorney, Agent, or Firm*—Kenyon & Kenyon

[57] ABSTRACT

Described is a process for removing glycerol and/or diglycerol from glycerides and glyceride mixtures by extraction, which process is characterized in that the glyceride or glyceride mixture is dissolved in organic compounds which preferably contain carbonyl and hydroxyl groups, if desired in combination with hydrocarbons, and that glycerol is extracted from the resulting solution with the aid of water. Thereby glycerol concentrations in the material to be purified of 0.1 weight % or lower may be obtained in a simple manner.

18 Claims, 1 Drawing Sheet

PROCESS FOR REMOVING GLYCEROL FROM GLYCERIDES

This application is a continuation of application Ser. No. 07/891,722 filed Jun. 1, 1992, now abandoned.

This application claims priority from German Patent Application No. P 41 18 487.4, filed on Jun. 5, 1991, which is hereby incorporated by reference.

The present invention relates to a process for removing glycerol and diglycerol resp. from glycerides which are contaminated therewith, in particular to a process in which the glycerol content of the glycerides may be reduced to 0.1 weight-% and lower, preferably to even 0.01 weight-% and lower.

Mono- and diglycerides have emulsifying, stabilizing, plastifying and thickening properties. Because the mono- and diesters of glycerol will fatty acids are edible they are used in various fields of foodstuff industry, for pharmaceuticals and cosmetics. The mixtures called glycerol monostearate, glycerol monooleate, glycerol monopalmitate etc. are water-in-oil-emulsifiers (W/O-emulsifiers). By small amounts of additives (soaps, polyethylene oxide compounds, sulfated alcohols) they become self-emulsifying and then are good oil-in-water emulsifiers (O/W-emulsifiers). Depending on the type of additive they are also able to provide acid-stable and (within certain limits) electrolyte-stable emulsions.

Monoglyccrides of higher fatty acids (e.g. glycerol monostearate) may also be used as lubricants in the processing of plastics. Monoglycerides obtained by molecular distillation and having a monoester content of more than 90% are mainly used in the foodstuff industry (doughs, confectionaries and baking auxiliary agents, margarine, ice cream). By reacting monoglycerides with acetic acid liquid to waxy monoglycerides (aceto glycerides) are obtained which may be used in foodstuffs (protective film), cosmetics and pharmaceuticals due to their compatiblity with pharmaceutical active components and their physiological harmlessness.

The addition of monoglyceride (up to 5% of palmitic/ stearic acid and 90 to 10% of palmitic-stearic acid mono-/ -diglyceride) achieves self-emulsifying properties in the baking fats intended for baking purposes (termed "superglycerolated shortenings").

Due to their specific structure monoglycerides are able to vary the plastifying action of starch and gluten in the preparation of dough by inserting in fine distribution into the homogenous plastified material, breaking it up and thus making the dough smoother, i.e. they shorten it. At the same time the incorporation of air is facilitated so that altogether baked goods having an enlarged volume and improved "shortness" are obtained.

Mono- and diglycerides are, in particular, obtainable by esterification of glycerol with fatty acids. Another method is the reaction of triglycerides with glycerol. More recently, also the enzymatic decomposition of triglycerides is intensely examined. During the esterification which is usually carried out at a higher temperature in the presence of a catalyst (e.g. a calcium or sodium soap) an equilibrium mixture of 60% of monoglycerides, 35% of diglycerides and 5% of triglycerides is obtained. By variation of the reaction conditions the yields of monoglycerides may be varied within wide ranges.

After cooling the reaction mixture the excess glyceride is removed as lower phase by decanting. In the upper phase which contains the glyceride mixture usually about 6 to 20 weight % of free glycerol and also 1 to 2 weight % of free fatty acids are dissolved. Glycerol (and possibly diglycerol) resulting from the reaction is removed before the products are marketed. In products which have been enriched with monoglycerides by molecular distillation the removal of the glycerol may also be effected after the distillation. The glycerol removal is effected by distillation and/or washing with water. Frequently, free glycerol is also removed by steam stripping at reduced pressure. In cases in which the glycerol is distilled off or stripped the catalyst remains in the glyceride mixture. The known processes are able to reduce the glycerol content to 1 to 2 weight-%. It was also suggested to wash out the glycerol with a 5% aqueous solution of NaCl (Bailey's Industrial Oil and Fat Products, Vol. 2, 4th Ed., John Wiley & Sons, New York, 1982, page 139). The wash method with water is difficult and altogether not satisfying because of the high surface activity of the material and the ease, with which emulsions are formed. In shortenings of the emulsifier-type only glycerides having a maximum content of free glycerol of 0.30 weight % are permitted as additive (6% of mono- and diglycerides).

When used in the field of foodstuffs the catalyst, in general, must be removed from the mixture of glycerides. This may be done by adsorption or by ion exchange. The mixture of glycerides is then further separated by molecular distillation. Thus products having a monoglyceride content of from 90 to 95 weight % are obtained. The accumulation of monoglycerides from products rich in lauric acid, as for example coconut oil or palm kernel oil, by distillation, is impaired by the fact that the diglycerides of short chain fatty acids (e.g. caproic acid, caprylic acid and caprinic acid) evaporate together with the monoglycerides of longer chain fatty acids.

At the high temperatures in the film evaporator disproportioning to a certain degree occurs leading to free fatty acids and glycerol. About 40% of the feed is obtained as a highly pure monoglyceride. During the molecular distillation the glycerol accumulates in the distillate. After the molecular distillation measures to reduce the content of glycerol and diglycerol, which are formed at the high temperatures in the film evaporator (usually about 200° to 220° C.), are therefore necessary.

Beside the mono- and diglycerides of $C_{18}$–$C_{16}$-fatty acids which are preferred in the foodstuff industry, for cosmetics, pharmaceuticals and for technical purposes, glycerides of fatty acids of shorter chain length have increasingly gained importance as starting materials in the preparation of biodegradable tensides. For this, palm kernel and coconut oils are used as starting materials. The following table summarizes the composition of fatty acids of several plant oils. The data are in percent, based on the overall content of the fatty acids.

| Fatty acid | Sunflower oil | Palm oil | Soybean oil | Coconut oil | Palm-kernel oil |
|---|---|---|---|---|---|
| Caproic acid | — | — | — | to 0.8 | to 0.2 |
| Caprylic acid | — | — | — | 7.8–9.5 | 2.7–4.3 |
| Caprinic acid | — | — | — | 4.5–9.7 | 3.0–7.0 |
| Lauric acid | — | — | — | 44–51 | 47–52 |
| Myristic acid | — | 0.6–2.4 | to 0.4 | 13–18.5 | 14–17.5 |
| Palmitic acid | 3.3–6.5 | 32–45 | 2.3–10.6 | 7.5–10.5 | 6.5–8.8 |
| Stearic acid | 1.3–3 | 4–6.3 | 2.4–6 | 1–3 | 1–2.5 |
| Oleic acid | 14–43 | 38–53 | 23.5–31 | 5–8.2 | 10.5–18.5 |
| Linoleic acid | 44–68 | 6–12 | 49–51.5 | 1–2.6 | 0.7–1.3 |

The removal of glycerol from the monoglycerides of fats rich in lauric acid (also termed "laurics") is more difficult than the removal of glycerol from the monoglycerides of stearic acid and oleic acid, because, with decreasing content of glycerol, increasingly more monoglycerides of short chain fatty acids are distilled off during the distillation so that the composition of fatty acids is changed.

Thus the present invention was based on the task to provide a process for the removal of glycerol and, if desired, diglycerol, from glycerides and glyceride mixtures contaminated therewith by extraction, which process, in particular, enables the content of (di)glycerol to be reduced to values of 0.1 weight % and lower, in particular to 0.1 to 0.01 weight %, and in which the problem of emulsion formation does not or only slightly occur during the extraction and which may be carried out continuously.

Therefore, subject matter of the invent on is a process for removing glycerol and/or diglycerol from glycerides and glyceride mixtures by extraction, which is characterized in that the glyceride or glyceride mixture is dissolved in (a) at least one organic compound having a carbonyl- and/or sulfoxide and/or sulfone group and a solubility in water of at most 15 weight %, preferably at most 10 weight %, (at 20° C.), and a boiling point of at most 200° C. (at normal pressure) (compound of type A), either as such or in admixture with up to 70 weight %, preferably up to 50 weight % and in particular up to 10 weight %, based on the mixture, of one or more compounds selected from compounds of type A with the exception that the solubility in water is more than 15 weight %, preferably more than 20 weight % (compound of type B), and hydroxyl group containing compounds having a boiling point of at most 200° C. (compound of type C); or (b) at least one compound of type A and/or at least one compound of type B and/or at least one compound of type C as defined above in admixture with 5 to 95, preferably 20 to 80 and in particular 40 to 60, weight %, based on the mixture, of one or more compounds from the group of optionally halosubstituted hydrocarbons having up to 20 carbon atoms (compound of type D), and ethers having up to 20 carbon atoms (compound of type E); or (c) at least one compound of type E either as such or in admixture with up to 80, preferably up to 70 and in particular up to 60, weight %, based on the mixture, of at least one compound of type D; or (d) carbon dioxide or a mixture of carbon dioxide with up to 95, preferably 20 to 80 and in particular 30 to 70, weight %, based on the mixture, of propane and/or butane, the amounts of solvents (a), (b), (c) or (d) being chosen so that a solution of 5 to 80, preferably 10 to 60 and in particular 20 to 40, weight % of the glyceride or glyceride mixture resp. to be purified is obtained in the solvent; and glycerol (diglycerol) being extracted from the resulting solution by means of water. (During this, soaps used as catalysts are extracted with the glycerol.)

The glycerides or glyceride mixtures to be purified according to the above process usually show an overall content of glycerol and diglycerol of 0.2 to 30, in particular 0.3 to 25 and more frequently 1 to 20, weight %. Most frequently the glycerol content is 5 to 17 weight %.

As mentioned above the substances which are to be freed from glycerol and diglycerol resp. according to the invention are monoglycerides, diglycerides or triglycerides or any mixture thereof. Of course, the monoglycerides as such may be present as mixtures of monoesters of glycerol with different fatty acids. Corresponding statements apply to diglycerides and triglycerides. As starting materials particularly preferred according to the invention are monoglycerides and diglycerides resp. and their mixtures.

The glyceride mixtures to be purified are preferably obtained by esterification of glycerol with carboxylic acids, transesterification of triglycerides with glycerol or enzymatic cleavage of triglycerides or fractionation of the thus obtained mixtures. In case of mixtures of mono-, di- and triglycerides they usually show the following composition, the percentages being based on the overall amount of glycerides and free (fatty) acids:

20 to 99, preferably 30 to 80 and in particular 40 to 70, weight % of monoglycerides;

0.4 to 95, preferably 15 to 60 and in particular 25 to 45, weight % of diglycerides;

0.3 to 20, preferably 1 to 15 and in particular 34 to 10, weight % of triglycerides;

0.3 to 5, in particular 0.5 to 3, weight % of free (fatty) acids.

The glycerides and glyceride mixtures to be purified according to the invention usually derive from (if desired unsaturated) aliphatic carboxylic acids (fatty acids) having 4 to 22, preferably 6 to 18, carbon atoms. Examples of such acids are butyric acid, caproic acid, caprylic acid, caprinic acid, lauric acid, myristic acid, palmitic acid, stearic acid, oleic acid, linoleic acid, linolenic acid and arachidonic acid.

In the following, the compounds used in solvents (a), (b), (c) and (d) are illustrated in detail.

Compounds of type A having a water solubility of at most 15 weight % (and preferably of at most 10 weight %) are e.g. esters, lactones, (preferably tertiary) amides, lactames, sulfoxides and sulfones. Such compounds may carry further functional groups, provided these groups cannot react under the extraction conditions with the compounds present in the starting material to be purified or at least not with the glycerides. Inspite of the presence of such functional groups, of course, the provisos of boiling point and solubility in water have to be fulfilled. Examples of suitable functional groups which may be additionally present are hydroxy, halo (in particular F, Cl and Br) and $NO_2$. However, it is preferred to use compounds of type A without additional functional groups. Of course the compounds of type A may also have several carbonyl, sulfoxide or sulfonic groups in the molecule. Examples of these are acetoacetic acid esters, acetyl acetone and alkyl esters of polyvalent carboxylic acids. According to the invention esters, lactones and ketones, in particular esters and lactones having altogether 4 to 8 carbon atoms, are preferred as compounds of type A; ethyl acetate, isopropyl acetate and butyl acetate are particularly mentioned of which ethyl acetate is particularly preferred, not only because of its physiological harmlessness.

The sense of the statements about the compounds of type A also applies to the compounds of type B, however considering, that the compounds of type B must show a water solubility of more than 15 weight %, preferably more than 20 weight % and in particular more than 50 weight %. Particularly preferred is an unlimited miscibility with water. Typical representatives of compounds having sulfonic or sulfoxide groups are dimethyl sulfoxide and sulfolane. Examples of amides are dimethyl formamide and dimethyl acetamide. Preferred representatives of the compounds of type B, however, are (cyclo)aliphatic ketones having altogether 3 to 6 carbon atoms, such as e.g. acetone, butanone, 3-pentanone and cyclohexanone. Particularly preferred are acetone and butanone.

The compounds of type C have at least one hydroxyl group and are preferably soluble in water to at least 20 weight %. Their maximum boiling point is 200° C., as that of the compounds of types A and B, in particular 160° C. maximum and preferably 130° C. maximum. Compounds of Types A, B and C having a boiling point below 100° C. are particularly preferred.

Beside the at least one hydroxyl group the compounds of type C may, of course, contain further functional groups; as to their reactivity under the extraction conditions the same applies as for the functional groups which may be additionally present in the compounds of types A and B. Among the compounds of type C there are, in particular, (cyclo)aliphatic alcohols and diols; in the diols one of the hydroxyl groups may, if desired, be etherified (e.g. with a $C_1$–$C_4$-alkyl group). The preferred number of carbon atoms in the compounds of type C is 1 to 6. Typical representatives of this class of compounds are methanol, ethanol, isopropanol, n-butanol and ethylene glycol as well as ethylene glycol monomethyl ether and ethylene glycol monoethyl ether. Particularly preferred among these compounds are methanol, ethanol, isopropanol and n-butanol, ethanol (and to a lesser extent also ispropanol) being favoured because it is permitted for the use in foodstuffs. Also in case of the compounds of type C it is particularly desirable when they are miscible with water in any ratio.

The compounds of type D are optionally halosubstituted hydrocarbons having up to 20 carbon atoms. Among the halogenated compounds those may be mentioned which have chlorine atoms, if desired, in combination with fluorine atoms. Typical representatives of these are methylene chloride, chloroform and tetracarbon chloride, as well as $CHFCl_2$ and $CCl_2F_2$. However, it is usually preferred to use compounds of type D which are free from halogen atoms. Although aromatic compounds, such as toluene, may be used the compounds of type D are preferably (cyclo)aliphatic. In general, they have 2 to 12 carbon atoms and preferably 2 to 7 carbon atoms. Preferred among these compounds are propane and butane because their use is permitted in foodstuffs. Commercially available butane predominantly consists of n-butane, which contains about 5 to 10 weight % of isobutane. Due to its good accessibility also commercially available isohexane (petroleum ether) may be used for non-foodstuff purposes. This isohexane is an isomeric mixture essentially consisting of hydrocarbons having 5 to 7 carbon atoms.

Although compounds of type D are preferably used in solvent (b) they may be fully or partly replaced according to the invention by compounds of type E. The compounds of type E are preferably (cyclo)aliphatic ethers having up to 20 carbon atoms, in particular 3 to 12 and preferably 4 to 8 carbon atoms. These ethers preferably contain 1 to 3 ether groups. Examples of these are diethyl ether, di(iso)propyl ether, tetrahydrofurane, dioxane, trioxane, ethylene glycol, dialkyl ether, and diethylene glycol dialkyl ethers (the alkyl groups preferably having 1 to 4 carbon atoms). Particularly preferred compounds of type E are diethyl ether, di(iso)propyl ether, tetrahydrofurane and dioxane.

The process according to the invention is preferably carried out with an amount of water which is the 1- to 8-fold, preferably the 2- to 5-fold, necessary to obtain a two-phase system (at least in the last extraction stage). The water for the extraction, of course, must not necessarily be pure water, but may contain dissolved therein (particularly inorganic) additives, such as salts, although this is usually not preferred. Only in the purification of a glyceride mixture, which has been obtained by enzymatic cleavage of triglycerides, it may be advantageous to basify the aqueous phase by an adequate additive, so that beside the glycerol also the free fatty acids are extracted from the mixture.

Especially when the process according to the invention is to be carried out continuously, which is preferred (in particular in the form of a countercurrent extraction) it is recommendable to use water which already contains an equilibrium concentration (±2 and preferably ±1%) of the compounds of types B and/or C (and optionally A), which would be formed during the course of the extraction in the aqueous phase. When the solvent is recovered after the extraction and recycled the equilibrium concentration builds up automatically in the course of time.

On principle, the process according to the invention may be carried out under all conditions of temperature and pressure. Generally the extraction process of the present invention is carried out at a temperature between 20° and 160° C. However, it is particularly preferred to effect the extraction at a temperature from room temperature up to the melting point (and, if desired, up to 10° C. above the melting point) of the glyceride mixture. Especially a process temperature close to the melting point of the glycerides guarantees that said glycerides do not start to separate during the extraction which may otherwise lead to problems, in particular when operating continuously. However, it has to be born in mind that glycerides are not infinitely temperature-stable so that temperatures essentially above the melting temperature of the glycerides are normally not recommended. The maximum process temperature is preferably 50° to 85° C., also depending on the thermal stability of the glycerides to be purified.

On principle, the process according to the invention may be carried out at normal pressure as well as at higher or lower pressures, depending on the solvent. However, when compounds are used as components of the solvent, which are gaseous at the process temperature under normal pressure, one must, of course, operate under excess pressure. This is particularly true when using solvent system (d), but also in case of solvents (b) and (c), when e.g. gaseous hydrocarbons are used as solvent components.

As mentioned above, glycerol concentrations of 0.1 weight % and lower may be easily obtained, so that no further measures for the glycerol removal, e.g. after concentrating the monoglycerides, are necessary. Furthermore the process according to the invention may be carried out at low temperatures at which a modification of the glycerides can be excluded. After effecting the process according to the invention the glycerides may be easily recovered according to the invention in yields above 98%.

When water is added e.g. to a solution of the glyceride mixture in a hydrocarbon, which contains a larger amount of an alkanol miscible with water in any ratio, in an amount so as to result in two coexisting phases, it was surprisingly observed that the lower phase contains almost completely the glycerol and diglycerol, while the upper phase contains the glyceride mixture. The distribution factor of glycerol and diglycerol between the lower and upper phases is surprisingly high (mostly higher than 10). The concentration of glycerides in the lower phase is low, so that only minor losses of monoglycerides occur during the extraction of the glycerol. The catalysts used preferably go into the lower phase. Usually (basic) salts, such as alkaline earth metal and alkali metal compounds, are used as catalysts. The content of catalysts in the glyceride or glyceride mixture is essentially reduced during the extraction according to the process of this invention. Most frequently, a separate process step for the removal of the catalysts from the end product is unnecessary.

Monoglycerides are only relatively little soluble in hydrocarbons. By the addition e.g. of alkanols which are highly soluble in water the solubility of the glycerides in hydrocarbons is so much increased that concentrations of up to 80 weight % may be easily obtained. The extraction of glycerol from a glyceride mixture with water is highly impaired by the tendency of forming an emulsion. The phase separation in the system occurs very slowly so that in practice the content of glycerol may be reduced to values of only about 1% by the extraction. By distillation or steam stripping under reduced pressure values of 0.3 weight % are achieved at great expense. The addition of a highly water-soluble alkanol to the hydrocarbon surprisingly not only increases the solubility of the monoglycerides in the hydrocarbon but also suppresses the emulsion formation during the extraction of the glycerol with water. This results in an important acceleration of phase separation after intense mixing in the quasi-quaternary system of hydrocarbon, alkanol, water and glyceride mixture. Although the alkanol distributes in almost equal portions in the coexisiting phases a high selectivity for the extraction of glycerol by the aqueous phase has been observed. Due to the rapid phase separation an economically favourable countercurrent extraction may be carried out which leads to glycerol contents of less than 0.1 weight % already after three theoretical separation steps when the starting concentration has been about 12 weight %.

The removal of glycerol from glyceride mixtures, which have been obtained by transesterification or enzymatic lipolysis, by washing with water is long known and partly technically used. Due to the formation of an emulsion, however, the process becomes unfavourable and a complete removal of the glycerol is thus impossible. In the process according to the invention surprisingly no formation of an emulsion occurs. The lower and the upper phases separate sufficiently rapidly to realize a multistep counter-current process. It is thus possible to reduce the glycerol content of the glycerides or glyceride mixture to values of less than 0.1 weight %.

In a multistep extraction process (di)glycerol may be removed essentially completely in a countercurrent with the aid of water which e.g. contains the equilibrium concentration of alkanol from a solution of a (di)glycerol containing glyceride mixture in a hydrocarbon containing an alkanol in the corresponding ratio to the glyceride concentration.

It should also be mentioned that the process according to the invention may be carried out without any problem batchwise as well as continuously. For this e.g. the extraction in a packed column in a countercurrent, in a column having rotating inserts, in a mixer extractor settler type, in a centrifugal extractor or in a sieve-plate column is suitable. With the exception of using a centrifugal extractor the effectivity of the extraction may be further improved by pulsation, although usually the pulsation may be carried out conveniently only with small amounts of material.

BRIEF DESCRIPTION OF THE DRAWINGS

The process of the invention will now be illustrated referring to FIG. 1 with the example of a (continuous) glycerol extraction using an alkanol/hydrocarbon solvent mixture.

The extraction takes place countercurrently in extractor 2. A mixture of alkanol and water as extractant for the glycerol is fed to the extractor. The glyceride mixture to be extracted (purified) is dissolved to a clear solution in an alkanol/hydrocarbon mixture in the feed tank and mixer 1. This solution is introduced into extractor 2 and passes the latter countercurrently to the extractant. The solution of the glyceride mixture freed from glycerol, the raffinate, leaves extractor 2 and is introduced into distillation column 3.

Figure 1:
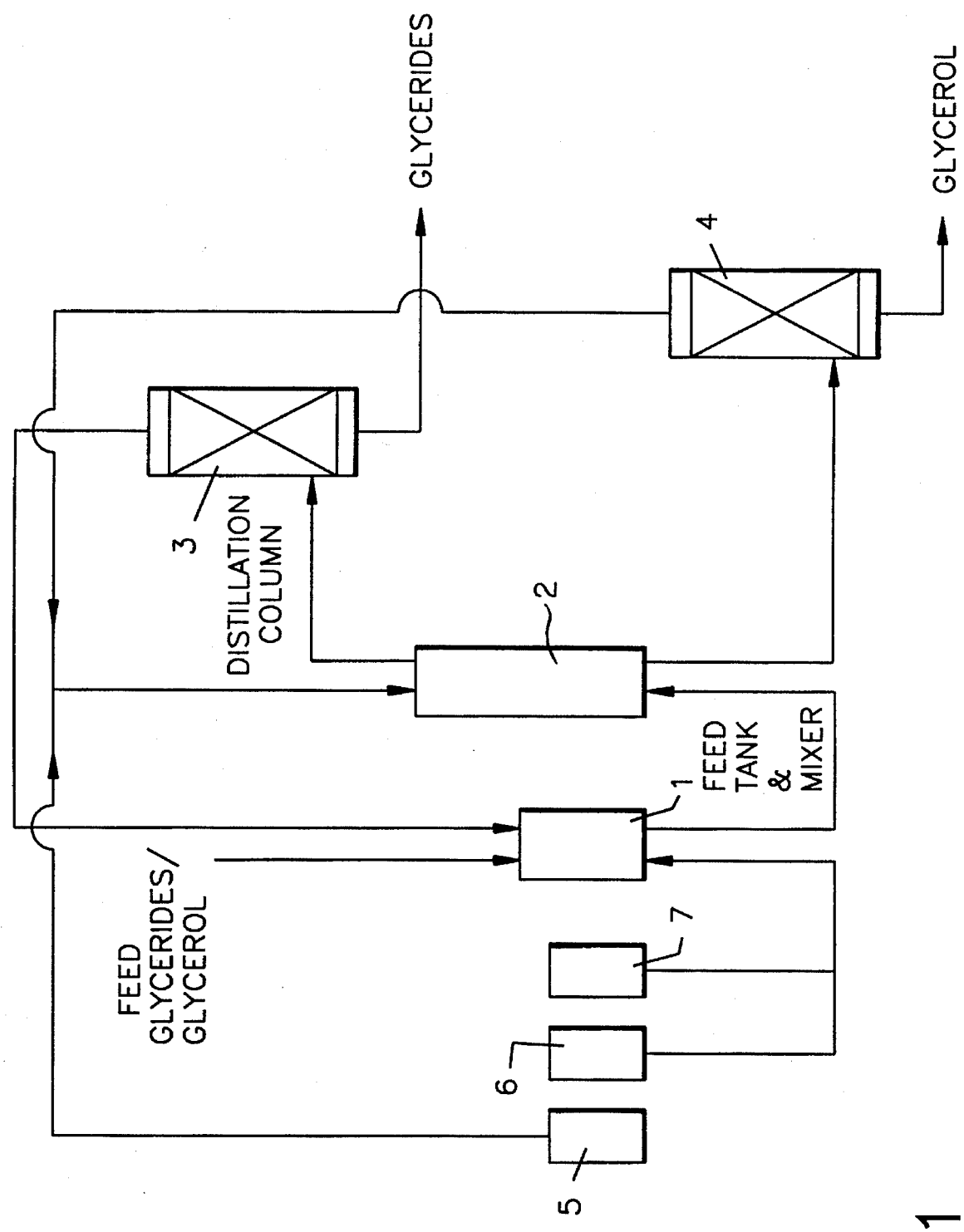

In the distillation column 3 the raffinate is separated into the solvent and the glyceride mixture by rectification. If the glycerides are temperature-sensitive the rectification is effected under reduced pressure. Beside alkanol and hydrocarbon the separated solvent contains some water which is dissolved in the raffinate. It is introduced into mixer 1. The glycerol-free glyceride or glyceride mixture is withdrawn from column 3 as bottom product.

The extract consists of a mixture of water, alkanol and glycerol which also contains minor amounts of glycerides and possibly free fatty acids and is introduced into distillation column 4. Water and alkanol are removed as head product from the glycerol by rectification, resulting in the bottom product of glycerol in which minor amounts of water and the glycerides which have passed into the extract are dissolved. The head product consisting of water and alkanol is introduced into extractor 2, eventual losses of water, alkanol and hydrocarbon from the storage tanks 5 (for $H_2O$), 6 (for hydrocarbons) and 7 (for alkanol) being balanced by pumping in from mixer 1.

The glyceride mixture or the glyceride to be processed is introduced into mixer 1 suitably in liquid form. Its temperature is thus above the respective melting temperature. After dissolution of the glycerides in the alkanol/hydrocarbon mixture the temperature, if desired, may be decreased and the extraction effected e.g. at room temperature. As mentioned above, there are essentially no limits with respect to the temperature at which the actual extraction occurs. Normally, however, a temperature range of 20° to 50° C. is preferred for the extraction of glycerol according to the process of the invention.

When e.g. propane or butane is used as hydrocarbon the extraction must be carried out under pressures which are equal to or slightly above the vapor pressure of propane or butane at the respective extraction temperature. For example the vapor pressure of propane is 8.5 bar at 20° C. and that of butane 2 bar.

The following examples serve to further illustrate the process according to the invention without restricting it. Unless stated differently, the percentages are based on the weight.

EXAMPLE 1

100 g of a mixture consisting of 64% of monoglycerides, 30% of diglycerides, 3.5% of triglycerides, 1% of free fatty acids and 1.5% of glycerol were dissolved at room temperature in a mixture consisting of 70 g of ethanol and 70 g of isooctane (commercial isomer mixture of hydrocarbons essentially having 7 to 9 carbon atoms) whereby a clear solution was formed. Then 150 g of water were added to this solution. After vigorous admixing two phases were formed within 30 minutes, the upper phase containing 97 g of the glyceride mixture and 0.3 g of glycerol, and the lower phase containing 3 g of the glyceride mixture and 1.2 g glycerol. This is equal to a separation factor of 129. After evaporating the lower phase a mixture containing 60.2% of glycerides remained. The ethanol was distributed approximately uniformly in the two phases.

EXAMPLE 2

100 g of a mixture consisting of 48.4 g of monoglycerides, 30.3 g of diglycerides and 5.1 g of triglycerides as well as 15.8 g of glycerol were dissolved in a mixture consisting of 70 g of ethanol and 70 g of isohexane (commercial isomer mixture of hydrocarbons essentially having 5 to 7 carbon atoms) whereby a clear solution was formed. This solution was vigorously admixed with 60 g of water. After settling two phases occurred, the upper phase containing 47.2 of monoglycerides, 29.3 g of diglycerides and 4.9 g of triglycerides as well as 1.8 g of glycerol. In a second extraction step the upper phase consisting of 81.4 g of glycerides, 1.8 g of glycerol, 70 g of isohexane, 8 g of ethanol and 9 g of water was treated and admixed with a mixture consisting of 60 g of water and 50 g of ethanol. When the two phases had settled an upper phase consisting of 78.6 g of glycerides, 0.09 g of free glycerol, 70 g of isohexane, 7 g of ethanol and 8 g of water was obtained.

In a third extraction step the upper phase from the second step was once more treated with a mixture consisting of 60 g of water and 50 g of ethanol. In the upper phase which formed after vigorous shaking and subsequent settling no glycerol could be detected even by capillary gas chromatography.

EXAMPLE 3

100 g of a mixture constisting of 58 g of monoglycerides, 35 g of diglycerides, 5.5 g of triglycerides, 1 g of free fatty acids and 0.44 g of glycerol were dissolved in a mixture consisting of 100 g of isohexane and 50 g of ethanol. Then 75 g of water were added to the solution, and the resulting system was thoroughly admixed. After settling two phases were formed the upper phase of which contained 98% of the glycerides employed and 24% of the introduced glycerol. 2% of the glycerides employed and 76% of the glycerol were present in the lower phase. The ratio by volume of the upper to the lower phases was about 3.4:1.

EXAMPLE 4

100 g of a mixture consisting of 58 g of monoglycerides, 36 g of diglycerides, 5.5 g of triglycerides, 1 g of free fatty acids and 0.44 g of glycerol were dissolved in 200 g of methanol and 200 g of isohexane. The solution was then mixed with 150 g of water and stirred. When stirring was interrupted two liquid phases of about equal volume were formed. The upper phase contained 98 g of the mixture added. Glycerol could no longer be detected in the upper phase, i.e. all the glycerol had been transferred into the lower phase.

EXAMPLE 5

157 g of a monostearate (0.35 g of glycerol, 0.36% of diglycerol, 1.03% of free fatty acids, 92.48% of monoglycerides, 0.32% of diglycerol-monoglyceride, 5.25% of diglycerides, 0.21% of triglycerides) were mixed at 60° C. and 6.5 bar with 303 g of ethanol, 333 g of butane and 362 g of water. After interrupting the mixing operation two liquid phases were formed. After evaporating the solvents, the components dissolved in the upper phase had the following composition: 0.10% of glycerol, 0.59% of free fatty acids, 99.31% of glycerides. Diglycerol could not be detected. After evaporating the solvents the components of the lower phase consisted of 18.46% of glycerol, 19.01% of diglycerol, 1.2% of free fatty acids and 62.53% of glycerides. Triglycerides could not be detected in the lower phase.

EXAMPLE 6

50 g of a mixture (from coconut oil) consisting of 56% of monoglycerides, 40% of diglycerides, 3.5% of free fatty acids and 0.44% of glycerol were dissolved in a mixture consisting of 125 g of isohexane and 125 g of isopropanol and then treated with 70 g of water. After interrupting the mixing operation two phases were formed the upper phase containing 16.0% and the lower phase containing 0.81% of the poorly volatile components. The phases had a volume ratio of about 5:1 and 98% of the glycerides employed were dissolved in the upper phase. After evaporating the solvents the glycerol content of the glycerides dissolved in the upper phase was 0.13%. 0.16 g of glycerol had been transferred to the lower phase (corresponding to a concentration of 2.67%, based on the poorly volatile dissolved material).

EXAMPLE 7

94 g of a mixture consisting of 46% of monoglycerides, 32% of diglycerides, 3.5% of triglycerides, 2% of diglycerol-monoglycerides, 1.2% of free fatty acids, 16.3% of free glycerol and 0.3% of diglycerol were introduced into a 1 1-autoclave together with 220 g of ethanol and 295 g of water. The autoclave was heated to 110° C., and then propane was pumped in with stirring at a pressure of 80 bar. Two phases were formed as could be observed through a window. Samples were taken from the upper and from the lower phases keeping the pressure constant by pumping in propane. The upper phase contained 74.5 g of the glyceride mixture and 0.75 g of free glycerol. Diglycerol could not be detected in the upper phase. The poorly volatile components in the upper phase thus contained 1.02% of free glycerol. The poorly volatile material in the lower phase consisted of 15.8 g of free glycerol, 0.3 g of diglycerol and 2.4 g of the glyceride mixture. Based on the poorly volatile material the content of free glycerol and diglycerol in the lower phase was 87%.

EXAMPLE 8

50 g of a mixture of stearic acid glycerides consisting of 58% of monoglycerides, 36% of diglycerides, 3.6% of triglycerides, 1% of free fatty acids and 1.4% of free glycerol were dissolved in a mixture consisting of 100 g of acetone and 100 g of isohexane and then admixed with 75 g of water. After interrupting the stirring operation two phases were formed, the upper phase containing 49 g of the poorly volatile material dissolved therein. This corresponds to 98% of the stearic acid glycerides employed. Free glycerol could not be detected in the upper phase even by gas chromatography. The lower phase contained 1 g of poorly volatile material, corresponding to 2% of the glyceride mixture employed. The content of free glycerol in the lower phase was 0.7 g or 70%, based on the content of poorly volatile material in the lower phase. The ratio by volume of the upper to the lower phase was about 1.6:1.

EXAMPLE 9

60 g of stearic acid glycerides (58% of monoglycerides, 36% of diglycerides, 3.6% of triglycerides, 1% of free fatty acids and 1.4% of free glycerol) were dissolved in a mixture consisting of 120 g of isohexane and 120 g of ethyl acetate and then treated with 66 g of water. After interrupting the mixing operation two phases were formed. The upper phase contained 56.2 g of dissolved poorly volatile components, corresponding to 94% of the product employed. Free glycerol could not be detected in the upper phase even by gas chromatography. The lower phase contained 3.8 g of poorly volatile components, corresponding to 6% of the starting material. The content of free glycerol in the lower phase was 22%, based on the poorly volatile material. The ratio by volume of the upper to the lower phase was about 3.6:1.

EXAMPLE 10

200 g of a glyceride mixture obtained from coconut oil (13,8 weight % of free glycerol) were vigorously admixed with 400 g of ethyl acetate and 200 g of water in a separating funnel. After completed phase separation the aqueous and the organic phases were worked up separately. The highly volatile solvents ethyl acetate and water were evaporated at 85° C. under a water jet vacuum. The content of poorly volatile material in the coexisting phases was 29.5 weight % in the upper phase and 16.5 weight % in the lower phase. The respective glycerol contents, based on the poorly volatile material, were 0.65 weight % in the upper phase and 75.2 weight % in the lower phase. This corresponds to a separation factor between glycerol and the glycerides of 0.00245. Therefore the amount of glycerides extracted together with the glycerol was very small. The glyceride losses were below 2% of the amount of glycerides employed.

EXAMPLE 11

100 g of a mixture of oleic acid glycerides (55% of monoglycerides, 32% of diglycerides, 3% of triglycerides, 1% of free fatty acids and 9% of free glycerol) were admixed with 80 g of $CO_2$ at 80° C. in a high pressure autoclave provided with a window. The pressure in the autoclave was 12 MPa. A highly liquid homogenous phase of glycerides and $CO_2$ was formed. Using a high pressure pump 25 g of water were dosed in and vigorously admixed with the $CO_2$-saturated glycerides for 10 minutes. After terminating the mixing operation the two phases separated very rapidly. One sample each was taken from the upper and the lower phase keeping the pressure in the autoclave constant by pumping in $CO_2$. The $CO_2$ dissolved in the samples was liberated during depressurisation and measured by means of a volume meter.

The water contained in the thus obtained samples was distilled off in a Vigreux column at 80° C. in a water jet vacuum. The amount of water was determined by differential weighing. The content of poorly volatile components in the upper phase was 55%. The lower phase contained 21% of poorly volatile components. The gas chromatographical analysis of the poorly volatile material showed that the glycerol content of the glycerides accumulated in the upper phase had been reduced to 2.0 weight %. The glycerol content in the poorly volatile material of the lower phase was 77 weight %. About 1.5% of the glycerides employed were dissolved in the lower phase. The advantage of this extraction system resides in the fact that only non-inflammable solvents are used.

EXAMPLE 12

100 g of a mixture obtained by glycerolysis consisting of 12.4 of glycerol and 87.6% of glycerides (60% of monoglycerides, the rest being diglycerides, triglycerides, free fatty acids) were treated with 200 g of dioxane and 200 g of isohexane in a shaking funnel. A water-clear homogenous liquid phase was formed. 200 g of water were added to extract the glycerol. The content of the shaking funnel was intensely admixed for 5 minutes. The subsequent settling time for the phase separation was only a few minutes. The aqueous lower phase and the organic upper phase were analysed, first evaporating the solvents. The content of poorly volatile material in the upper phase was 25.3%. The lower phase contained 5.5% of poorly volatile material. The glycerol content in the poorly volatile material of the upper phase was reduced to 0.58% by the extraction. The glycerol content in the poorly volatile material of the lower phase was 72.1%. About 4% of the glycerides were dissolved in the lower phase.

EXAMPLE 13

1000 g of a g glyceride mixture obtained from palm kernel oil having a glycerol content of 10.8% was admixed with 2000 g of tetrahydrofurane and 2000 g of isohexane in the feed vessel of the three-stage mixer extractor settler type. A clear highly liquid solution was rapidly formed. In the extractant vessel altogether 2000 g of $H_2O$ were provided. The solution to be extracted and the extractant were dosed into the extractor by means of centrifugal pumps. The two phases were guided countercurrently. Altogether 2400 g of glycerol-rich raffinate solution and 4600 g of extract solution were obtained. The solvents were evaporated from the extract and the raffinate. The content of poorly volatile material in the extract solution was 19.2% and in the raffinate solution 5.0%. Based on the glycerides the glycerol content in the extract was less than 0.1% and in the raffinate 90%. The glycerides extracted together with the glycerol were 1.3% of the glycerides employed.

EXAMPLE 14

100 g of a glyceride mixture obtained from coconut oil having a glycerol content of 12.7% were mixed with 300 g of diisopropyl ether in a separating funnel. After the addition of water (300 g) and intense admixing two phases were formed within a few minutes. At first the lower phase was still turbid. After a resting time of several hours the turbidity had disappeared. The two phases were worked up separately. Distilling off the ether and water resulted in a content of poorly volatile material in the upper phase of 22% and in the lower phase of 6.0%. The glycerol concentrations in the poorly volatile material were 0.18% in the upper phase and 71% in the lower phase. The ratio by volume between the upper and the lower phase was about 1.24:1.

EXAMPLE 15

100 g of oleic acid glycerides (55% of monoglycerides, 35% of diglycerides, 3% of triglycerides, 2% of free fatty acids and 5% of free glycerol) were admixed with 70 g of a mixture consisting of 51 weight % of $CO_2$ and 49 weight % of $C_3H_8$ at 60° C. in a high pressure autoclave provided with a window. The pressure in the autoclave was 60 bar. A highly liquid homogenous phase consisting of glycerides, propane and $CO_2$ was formed. By means of a high pressure pump 130 g of water were dosed in and thoroughly admixed with the gas-saturated glycerides for 10 minutes. After terminating the mixing operation the two phases formed very rapidly. One sample each was taken from the upper and the lower phases, keeping the pressure in the autoclave constant by pumping in the gas mixture. The gas dissolved in the samples was liberated during depressurisation and measured by means of a volume meter. The water contained in the obtained samples was distilled off in a Vigreux column at 80° C. in a water jet vacuum. The amount of water was determined by differential weighing. The content of poorly volatile components in the upper phase was 41%. According to gas chromatographical analysis of the poorly volatile material the glycerol content of the glycerides accumulated in the upper phase had been reduced to 0.8%. The glycerol content of the poorly volatile material in the lower phase was 93%. About 0.3% of the glycerides employed were dissolved in the lower phase.

We claim:
1. Process for removing glycerol and/or diglycerol from glycerides or glyceride mixtures by liquid-liquid extraction carried out under subcritical conditions, characterized in that the glyceride or glyceride mixture is dissolved in a solvent selected from the group consisting of:

solvent (a) consisting of:
i. 30 to 100 weight %, based on the admixture, of at least one organic compound having at least one functional group selected from the group consisting of a carbonyl group; a sulfoxide group, a sulfone group, or a combination thereof and a solubility in water of at most 15 weight % and a boiling point of at most 200° C. in mixture with:
ii. 0 to 70 weight %, based on the admixture, of at least one organic compound having a carbonyl and/or sulfoxide and/or sulfone group and a solubility in water of more than 15 weight %, and
iii. 0 to 70 weight %, based on the admixture, of at least one compound containing a hydroxyl group and having a boiling point of at most 200° C.;

solvent (b) consisting of:
i. 5 to 95 weight %, based on the admixture, of at least one compound selected from the group of compounds set forth in (a), in mixture with:
ii. 5 to 95 weight %, based on the admixture, of at least one compound, having up to 20 carbon atoms, selected from the group consisting of hydrocarbons, halosubstituted hydrocarbons, ethers and combinations thereof;

solvent (c) consisting of:
i. 20 to 100 weight %, based on the admixture, of at least one ether having up to 20 carbon atoms, in mixture with:
ii. 0 to 80 weight %, based on the mixture, of at least one compound, having up to 20 carbon atoms, selected from the group consisting of hydrocarbons, halosubstituted hydrocarbons, and combinations thereof; and solvent (d) consisting of:
i. 5 to 100 weight %, based on the admixture, of carbon dioxide, in mixture with:
ii. 0 to 95 weight %, based on the admixture, of propane, butane, or both propane and butane;

the amounts of said solvent (a), (b), (c) or (d) being chosen so that the amount of the glycerides, or glyceride mixture, to be purified is 5 to 80 weight % of the resulting solution, and the glycerol, diglycerol or both is extracted from said resulting solution with the aid of water.

2. Process according to claim 1, further characterized in that the glyceride or glyceride mixture to be purified shows an overall content of glycerol and diglycerol of from 0.2 to 30 weight %.

3. Process according to claim 1, further characterized in that the glyceride mixture to be purified has been obtained by esterification of glycerol with carboxylic acids, by transesterification of triglycerides with glycerol, by enzymatic cleavage of triglycerides or by fractionation of the resulting mixtures and shows the following composition, each based on the overall amount of glycerides and free acids:

20 to 99 weight % of monoglycerides;
0.4 to 95 weight % of diglycerides;
0.3 to 20 weight % of triglycerides;
0.3 to 5 weight % of free fatty acids.

4. Process according to claim 1, further characterized in that the glycerides or the glyceride mixtures are derived from optionally unsaturated aliphatic carboxylic acids (fatty acids) having 4 to 22 carbon atoms.

5. Process according to claim 1, further characterized in that the compounds of types (a)i., (a)ii. and (a)iii. have a boiling point of at most 160° C.

6. Process according to claim 1, further characterized in that the ratio of water to the glyceride solution is adjusted so that the amount of water is the 1- to 8-fold of the amount which is necessary to obtain two phases in the final extraction stage.

7. Process according to claim 6, further characterized in that the water used for the extraction already contains the equilibrium concentration ±2% of the compounds of types (a)ii. and/or (a)iii. which would be formed in the aqueous phase in the course of the extraction.

8. Process according to claim 1, further characterized in that it is carried out continuously.

9. Process according to claim 1, further characterized in that it is carried out at temperatures of from 20° to 160° C.

10. Process according to claim 1, further characterized in that the extraction is carried out in a packed column in a countercurrent, in a column having rotating inserts, in a mixer extractor settler type, in a centrifugal extractor or in a sieve-plate column.

11. Process according to claim 1, further characterized in that:

the compounds of (a)i. consist of esters, lactones and ketones having a solubility in water of no more than 10 weight %;

the compounds of (a)ii. and iii., together, constitute 0 to 10 weight % of solvent (a);

the compounds of (b) ii. constitute 40 to 60 weight % of solvent (b);

the compounds of (c)ii. constitute 0 to 60 weight % of solvent (c); and propane, butane, or a combination thereof, constitute 30 to 70 weight % of solvent (d).

12. Process according to claim 11 further characterized in that said process is operated at a pressure of between 2 and 70 bar.

13. Process according to claim 1, further characterized in that:

the compounds of (a)i. consist of aliphatic esters, lactones, and combinations thereof, said esters and lactones having 4 to 8 carbon atoms;

the compounds of (a)ii. consist of (cyclo) aliphatic ketones having 3 to 6 carbon atoms;

the compounds of (a)iii. consist of monovalent, divalent, combinations of monovalent and divalent (cyclo) aliphatic alcohols having 1 to 6 carbon atoms;

at least one of the compounds of (b) ii. consist of (cyclo) aliphatic hydrocarbons having 2 to 12 carbon atoms or (cyclo) aliphatic ethers having 3 to 10 carbon atoms and 1 to 3 ether groups.

14. Process according to claim 1, further characterized in that:

the compounds of (a)i. consist of ethyl acetate, isopropyl acetate, butyl acetate, and mixtures thereof;

the compounds of (a)ii. consist of acetone, butanone, 4-pentanone, and mixtures thereof;

the compounds of (a)iii. consist of methanol, ethanol, isopropanol, n-butanol, ethylene glycol, and mixtures thereof;

the compounds of (b)ii. consist of propane, butane, isohexane, diethyl ether, di(iso)propyl ether, tetrahydrofuran, dioxane, and mixtures thereof.

15. Process according to claim 1, further characterized in that the compounds of type (a)i. are selected from ethyl acetate, isopropyl acetate and butyl acetate; and/or the compounds of type (a)ii. are selected from acetone, butanone and 4-pentanone; and/or the compounds of type (a)iii. are selected from methanol, ethanol, isopropanol, n-butanol and ethylene glycol; and/or the compounds of type (b)ii. are selected from propane, butane, isohexane, diethyl ether, di(iso)propyl ether, tetrahydrofuran and dioxane and their mixtures.

16. Process according to claim 8, further characterized in that it is carried out in a countercurrent.

17. Process for removing glycerol and/or diglycerol from glycerides or glyceride mixtures by liquid-liquid extraction carried out under subcritical conditions, characterized in that the glyceride or glyceride mixture is dissolved in a solvent selected from:

(i) at least one compound having a carbonyl and/or sulfoxide and/or sulfone group and a boiling point of at most 200° C. and/or a compound containing a hydroxyl group and having a boiling point of at most 200° C.;

(ii) in mixture with 95 to 5 weight %, based on the admixture, of one or more;
  (a) hydrocarbons or halogenated hydrocarbon having up to 20 carbon atoms, and;
  (b) ethers having up to 20 carbon atoms, the amount of said solvent being chosen to that a solution of the glycerides or glyceride mixture to be purified of 5 to 80 weight % in the solvent is obtained, wherein said glyceride mixture is separated from said solvent with the aid of water.

18. Process for removing glycerol and/or diglycerol from glycerides or glyceride mixtures by liquid-liquid extraction carried out under subcritical conditions, characterized in that the glyceride or glyceride mixture is dissolved in a solvent selected from:

(i) at least one compound having a carbonyl and/or sulfoxide and/or sulfone group and a boiling point of at most 200° C. and/or methanol and/or ethanol;

(ii) in mixture with 95 to 5 weight %, based on the admixture, of one or more;
  (a) propane
  (b) butane; and
  (c) ethers having up to 20 carbon atoms;

the amount of said solvent being chosen so that a solution of the glycerides or glyceride mixture to be purified of 5 to 80 weight % in the solvent is obtained, wherein said glyceride mixture is separated from said solvent with the aid of water.

* * * * *